US00PP14813P2

(12) United States Plant Patent
Bergman

(10) Patent No.: US PP14,813 P2
(45) Date of Patent: May 25, 2004

(54) CHRYSANTHEMUM PLANT NAMED 'YOJAMESTOWN'

(50) Latin Name: *Chrysanthemum×morifolium*
Varietal Denomination: Yojamestown

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 12 days.

(21) Appl. No.: 10/396,680

(22) Filed: Mar. 25, 2003

(51) Int. Cl.[7] ..... A01H 5/00

(52) U.S. Cl. ..... Plt./292

(58) Field of Search ..... Plt./292

*Primary Examiner*—Bruce R. Campell
*Assistant Examiner*—Anne Marie Grunberg
(74) *Attorney, Agent, or Firm*—C. A. Whealy

(57) ABSTRACT

A distinct cultivar of Chrysanthemum plant named 'Yojamestown', characterized by its uniform, upright and somewhat outwardly spreading plant habit; strong and freely branching growth habit; dark green-colored foliage; uniform flowering habit; early flowering habit; numerous decorative-type inflorescences; red purple-colored ray florets; and good postproduction longevity with plants maintaining good substance and color for about three weeks in an interior environment.

1 Drawing Sheet

Botanical classification/cultivar designation: *Chrysanthemum×morifolium* cultivar Yojamestown.

BACKGROUND OF THE INVENTION

The present Invention relates to a new and distinct cultivar of Chrysanthemum plant, botanically known as *Chrysanthemum×morifolium* and hereinafter referred to by the name 'Yojamestown'.

The new Chrysanthemum is a product of a planned breeding program conducted by the Inventor in Salinas, Calif. and Fort Myers, Fla. The objective of the breeding program is to create new compact potted Chrysanthemum cultivars that are suitable for year-round production with uniform plant growth habit, good vigor, desirable inflorescence form and floret colors, fast response time, and good postproduction longevity.

The new Chrysanthemum originated from a cross made by the Inventor in March, 1998, in Salinas, Calif., of a proprietary Chrysanthemum seedling selection identified as code number YB-5908, not patented, as the female, or seed, parent with a proprietary Chrysanthemum seedling selection identified as code number YB-4779, not patented, as the male, or pollen, parent. The new Chrysanthemum was discovered and selected by the Inventor as a single flowering plant within the progeny of the stated cross grown in a controlled environment in Fort Myers, Fla. in March, 1999. The selection of this plant was based on its uniform plant growth habit, desirable inflorescence form and ray floret colors, fast response time, and excellent postproduction longevity.

Asexual reproduction of the new Chrysanthemum by vegetative tip cuttings was first conducted in Fort Myers, Fla. in June, 1999. Asexual reproduction by cuttings has shown that the unique features of this new Chrysanthemum are stable and reproduced true to type in successive generations.

SUMMARY OF THE INVENTION

The cultivar Yojamestown has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yojamestown'. These characteristics in combination distinguish 'Yojamestown' as a new and distinct Chrysanthemum:

1. Uniform, upright and somewhat outwardly spreading plant habit.
2. Strong and freely branching growth habit.
3. Dark green-colored foliage.
4. Uniform flowering habit.
5. Early flowering, 8-week response time.
6. Numerous decorative-type inflorescences.
7. Red purple-colored ray florets.
8. Good postproduction longevity with plants maintaining good substance and color for about three weeks in an interior environment.

Plants of the new Chrysanthemum differ primarily from plants of the female parent selection in ray floret coloration as plants of the new Chrysanthemum have red purple-colored ray florets whereas plants of the female parent selection have light pink-colored ray florets. In addition, plants of the new Chrysanthemum have larger leaves and inflorescences than plants of the female parent selection.

Plants of the new Chrysanthemum differ primarily from plants of the male parent selection in ray floret coloration as plants of the new Chrysanthemum have red purple-colored ray florets whereas plants of the male parent selection have dark bronze-colored ray florets. In addition, plants of the new Chrysanthemum are more freely branching and have smaller inflorescences than plants of the male parent selection.

Plants of the new Chrysanthemum can be compared to plants of the cultivar Dark Pomona, disclosed in U.S. Plant Pat. No. 7,842. In side-by-side comparisons conducted in Salinas, Calif., plants of the new Chrysanthemum differed from plants of the cultivar Dark Pomona in the following characteristics:

1. Plants of the new Chrysanthemum were more compact than plants of the cultivar Dark Pomona.
2. Plants of the new Chrysanthemum had darker green-colored leaves than plants of the cultivar Dark Pomona.
3. Plants of the new Chrysanthemum flowered about one week earlier than plants of the cultivar Dark Pomona.
4. Plants of the new Chrysanthemum had smaller inflorescences than plants of the cultivar Dark Pomona.
5. Ray florets of plants of the new Chrysanthemum were darker red purple in color than ray florets of plants of the cultivar Dark Pomona.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a side perspective view of typical flowering plants of 'Yojamestown' grown as spray-types.

The photograph at the bottom of the sheet comprises a close-up view of typical inflorescences of 'Yojamestown' grown as spray-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the fall in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 21 days later. At the time of the pinch, the photoinductive short day/long night treatments were initiated. Plants used for the photographs and description were grown as spray-types. Measurements and numerical values represent averages of typical flowering plants.

Botanical classification: *Chrysanthemum×morifolium* cultivar Yojamestown.

Commercial classification: Decorative-type potted Chrysanthemun.

Parentage:

*Female, or seed, parent.*—Proprietary *Chysanthemum×morifolium* seedling selection identified as code number YB-5908, not patented.

*Male, or pollen, parent.*—Proprietary *Chrysanthemum×morifolium* seedling selection identified as code number YB-4779, not patented.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous decorative-type potted Chrysanthemum that is typically grown as a spray-type. Uniform with lateral branches upright and somewhat outwardly spreading; uniformly mounded crown. Strong and freely branching growth habit; about four lateral branches develop after removal of terminal apex (pinching); dense and full plants.

*Plant height.*—About 30 cm.

*Plant width.*—About 46 cm.

*Lateral branches.*—Length: About 28 cm. Diameter: About 5 mm. Internode length: About 1.8 cm. Strength: Strong. Texture: Pubescent. Color: Close to 146A.

*Foliage description.*—Arrangement: Alternate; simple. Length: About 6.9 cm. Width: About 5.5 cm. Apex: Cuspidate. Base: Truncate. Margin: Palmately lobed, sinuses between lateral lobes parallel to overlapping. Texture, upper surface: Sparsely pubescent. Texture, lower surface: Pubescent; veins prominent. Color: Developing and fully expanded foliage, upper surface: 147A. Developing and fully expanded foliage, lower surface: Darker than 147B. Venation, upper and lower surfaces: 147B. Petiole length: About 1.8 cm. Petiole diameter: About 3 mm. Petiole color, upper and lower surfaces: 147B to 147C.

Inflorescence description:

*Appearance.*—Decorative-type inflorescence form with elongated oblong-shaped ray florets. Inflorescences borne on terminals above foliage. Disk and ray florets develop acropetally on a capitulum. Inflorescences not fragrant. Plants are typically grown as spray-types.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to three weeks of long day/short night conditions followed by photoinductive short day/long night conditions flower about eight weeks later.

*Postproduction longevity.*—Inflorescences maintain good color and substance for about three weeks in an interior environment.

*Quantity of inflorescences.*—Freely flowering, about 14 inflorescences develop per lateral branch.

*Inflorescence bud.*—Height: About 5.5 mm. Diameter: About 6 mm. Shape: Oblate. Color: Close to 147A.

*Inflorescence diameter.*—About 5.75 cm.

*Inflorescence depth (height).*—About 2.2 cm.

*Diameter of disc.*—About 2 mm, inconspicious.

*Receptacle diameter.*—About 4 mm.

*Ray florets.*—Shape: Elongated oblong. Orientation: Initially upright, eventually perpendicular to the peduncle. Aspect: Initially incurved, then flat.

Length: About 3 cm. Corolla tube length: About 4 mm. Width: About 1 cm. Apex: Rounded to emarginate. Base: Fused into a corolla tube. Margin: Entire. Texture: Smooth, glabrous, velvety. Number of ray florets per inflorescence: About 165 in numerous whorls. Color: When opening and fully opened, upper surface: Close to 71A; color becoming close to 78C with development. When opening and fully opened, lower surface: Close to 155D underlain with 71A to close to 77A.

*Disc florets.*—Arrangement: Massed at center of receptacle. Shape: Tubular, elongated. Apex: Five-pointed. Length: About 3.5 mm. Diameter, apex: About 1 mm. Diameter, base: About 1 mm. Number of disc florets per inflorescence: About 12. Color: Immature: Close to 9A. Mature: Apex: 9A. Mid-section: 17A. Base: Close to 155D.

*Peduncles.*—Length: First peduncle: About 2.25 cm. Fourth peduncle: About 5 cm. Seventh peduncle: About 8.1 cm. Diameter: About 2.25 mm. Angle to vertical: About 45° from vertical. Strength: Strong, flexible. Texture: Pubescent. Color: 146A.

*Phyllaries.*—Quantity per inflorescence: About 22. Length: About 6 mm. Width: About 3 mm. Shape: Deltoid. Apex: Acute. Base: Truncate. Margin: Entire. Texture, upper surface: Waxy, smooth. Texture, lower surface: Pubescent. Color, upper and lower surfaces: 147A.

*Reproductive organs.*—Androecium: Present on disc florets only. Anther color: Close to 9A. Pollen amount: None observed. Gynoecium: Present on both ray and disc florets. Style color: Close to 144B to 144C. Sitgma color: Close to 9A.

*Seed/fruit.*—Seed and fruit production has not been observed.

Disease/pest resistance: Resistance to pathogens and pests common to Chrysanthemums has not been observed on plants grown under commercial greenhouse conditions.

It is claimed:

1. A new and distinct cultivar of Chrysanthemum plant named 'Yojamestown', as illustrated and described.

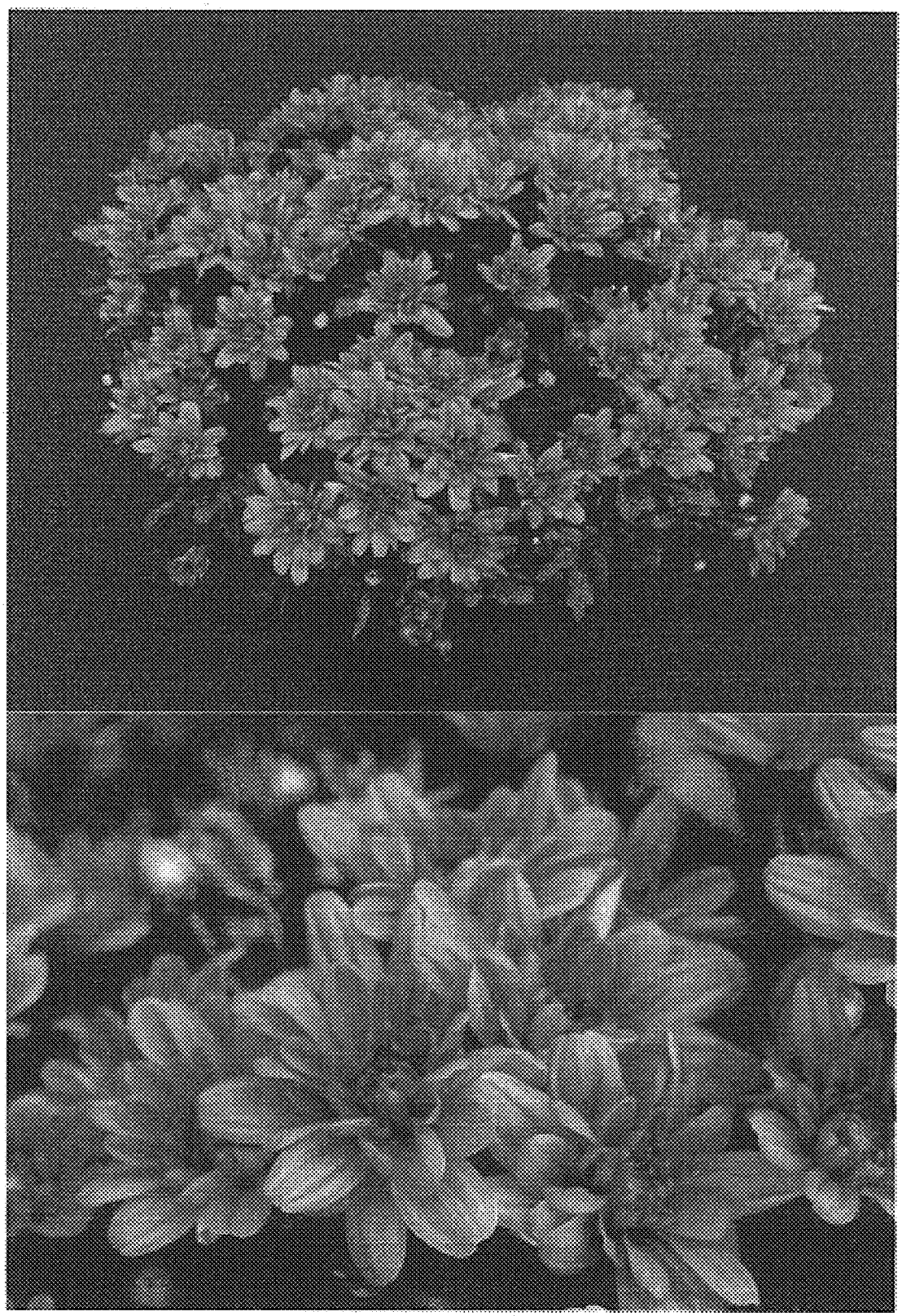

* * * * *